United States Patent [19]
Chase et al.

[11] Patent Number: 5,778,041
[45] Date of Patent: Jul. 7, 1998

[54] SYSTEM AND PROCESS FOR MEASURING ASH IN PAPER

[75] Inventors: Lee Chase, Los Gatos; John Goss; Philip Hegland, both of San Jose, all of Calif.

[73] Assignee: Honeywell-Measurex Corporation, Cupertino, Calif.

[21] Appl. No.: 9,406

[22] Filed: Jan. 27, 1993

Related U.S. Application Data

[63] Continuation of Ser. No. 892,595, May 28, 1992, abandoned, which is a continuation of Ser. No. 552,338, Jul. 12, 1990, abandoned, which is a continuation of Ser. No. 274,645, Nov. 17, 1988, abandoned, which is a continuation of Ser. No. 541,622, Oct. 13, 1983, abandoned.

[51] Int. Cl.$^6$ ........................................ G01N 23/06
[52] U.S. Cl. ........................................ 378/53; 378/51
[58] Field of Search ........................................ 378/53

[56] References Cited

U.S. PATENT DOCUMENTS

| | | |
|---|---|---|
| Re. 30,884 | 3/1982 | Buchnea . |
| 2,445,305 | 7/1948 | Hochgesang . |
| 2,861,188 | 11/1958 | Dijkstra . |
| 2,983,819 | 5/1961 | Bigelow et al. . |
| 3,030,512 | 4/1962 | Harker . |
| 3,100,261 | 8/1963 | Bigelow ........................... 378/53 |
| 3,114,832 | 12/1963 | Alvarez ........................... 378/53 |
| 3,121,166 | 2/1964 | Vossberg . |
| 3,270,204 | 8/1966 | Rhodes . |
| 3,287,560 | 11/1966 | Morgan . |
| 3,366,790 | 1/1968 | Zagorites et al. . |
| 3,402,292 | 9/1968 | Baecklund . |
| 3,412,249 | 11/1968 | Hanken . |
| 3,417,244 | 12/1968 | Kramer . |
| 3,435,220 | 3/1969 | Hanken . |
| 3,452,192 | 6/1969 | Hanken . |
| 3,525,863 | 8/1970 | Constantine et al. . |
| 3,530,296 | 9/1970 | Lehtinen et al. . |
| 3,581,087 | 5/1971 | Brinkerhoff et al. . |
| 3,701,899 | 10/1972 | Voparil . |
| 3,843,884 | 10/1974 | Evans . |
| 3,904,876 | 9/1975 | Arendt ........................... 378/53 |
| 4,081,676 | 3/1978 | Bachnea ........................... 378/53 |
| 4,090,074 | 5/1978 | Watt et al. . |
| 4,168,431 | 9/1979 | Henriksen . |
| 4,363,968 | 12/1982 | McGowan et al. . |
| 4,815,116 | 3/1989 | Cho . |

FOREIGN PATENT DOCUMENTS

| | | |
|---|---|---|
| 1859276 | 10/1976 | Australia . |
| 48-16877 | 3/1973 | Japan . |
| 958240 | 5/1964 | United Kingdom . |
| 2044443 | 10/1980 | United Kingdom . |
| WO8301113 | 3/1983 | WIPO . |

OTHER PUBLICATIONS

"A New TiO$_2$ Compensated X-Ray Ash Sensor for Paper", by B.Y. Cho and O.L. utt, Industrial Nucleonics, Columbus, Ohio, 1975.

"Composition Compensated Paper Ash Gauge", by Orval I. Utt and Hoong Y. Cho Industrial Nucleonics Corporation, Columbus, Ohio, 1975.

Co-pending and Commonly-Assigned U.S. Patent Application No. 06/549,026 to Hegland, et al, filed Nov. 7, 1983.

Alexander Buchnea, Lawrence A. McNelles and John S. Hewitt, *The Application of X-Ray Absorption and Fluorescence Analysis to the Measurement of Paper Additives*, Int.J.Appl.Radiat.Isot. vol. 33, pp. 285 to 292 (1982).

(List continued on next page.)

*Primary Examiner*—Craig E. Church
*Attorney, Agent, or Firm*—Loeb & Loeb LLP

[57] ABSTRACT

A system and process are provided for determining the concentration of a first component of a mixture wherein the first component includes at least 3 materials. The process includes directing 2 beams of x-rays into the mixture and receiving portions of the beams which are transmitted through the mixture. The concentration of the first component is determined based upon the beams transmitted through the mixture.

25 Claims, 2 Drawing Sheets

OTHER PUBLICATIONS

Nils C. Fernelius, Richard J. Harris, David B. O'Quinn, Michael E. Gangl and David V. Dempsey, *Some optical properties of materials measured at 1.3 μm*, 2417 Optical Engineering, vol. 22, pp. 411–418 (1983).

*Abstracts of papers to be Presented at the ERDA Symposium on X–and Gamma–Ray Sources and Applications*, May 19–21, 1976, Ann Arbor, Michigan, pp. 6,7,37.

Paul Kirkpatrick, *On the Theory and Use of Ross Filters*, Review of Scientific Instruments, pp. 186–191 (Jun., 1939).

SYSTEM AND PROCESS FOR MEASURING ASH IN PAPER

This is a continuation of 07/892,595 filed May 28, 1992 now abandoned which is a continuation of 07/552,338 filed Jul. 12, 1990 now abandoned which is a continuation of 07/274,645 filed Nov. 17, 1988 now abandoned which is a continuation of 06/541,622 filed Oct. 13, 1983 now abandoned.

BACKGROUND OF THE INVENTION

1. The Field of The Invention

The present invention relates to apparatus and process for measuring the percentage of ash in paper.

2. Description of the Prior Art

Paper and similar materials such as box board and corrugated board include wood material called fiber and other material called ash. Generally speaking, ash is defined as the residue remaining after complete combustion of paper. Ash can include various materials. Many paper manufacturers use clay, titanium dioxide or calcium carbonate; and in some cases barium sulfate and talc also comprise ash. In some cases only one of these materials will be used, whereas some manufacturers use mixtures of these materials, a common combination being clay and titanium dioxide or clay and calcium carbonate. During the manufacture of paper, it is important to control the ash content of the paper. The concentration of ash can affect the strength of the paper and also certain qualities such as printability. Furthermore, clay, which is often a component of ash, is generally far cheaper than wood fiber. Therefore, it is often important to maintain the ash content as high as reasonably possible while still maintaining other characteristics of the paper within specification.

The percentage of ash can be controlled manually by setting the rates of flow of clay and other ash stock as well as the flow of wood fiber to the paper making system and periodically sampling the paper to determine the value of ash in a laboratory. When the ash content is determined in the laboratory, the paper is burned under predetermined conditions and the resulting ash is weighed. This procedure of manual control suffers from the main disadvantage that it is time consuming and can result in the production of large quantities of paper which do not meet specifications.

An automated system to determine the percentage of ash relies upon the selective absorption of x-rays. The transmission of x-rays through paper can be characterized by Beer's Law:

$$R = I \div I(O) = e^{-\mu W}$$

Where $\mu$ is the mass absorption coefficient and $W$ is the weight of the paper. $I$ is the intensity of the x-rays through the sample and $I(O)$ is the intensity of the x-rays without the sample present.

The mass absorption coefficient, $\mu$, can be viewed as the sum of the products of the individual mass absorption coefficients of each constituent and their respective weight fractions.

$$\mu = \sum_{i=1}^{N} \mu_i W_i$$

The paper can be understood to consist of fiber and ash, and therefore:

$$\mu = \mu_f W_f + \mu_a W_a$$

Thus, when $\mu_f$ and $\mu_a$ are known, the percentage of ash can be determined.

The system for accomplishing this includes a source of x-rays mounted on one side of a sheet of paper and an x-ray detector mounted on the other side of the paper to receive x-rays which are transmitted through the paper. The detector is coupled to an electronic system to measure the intensities $I$ and $I(o)$ and a computer is coupled to the electronics to carry out the necessary calculations. Such a system is generally satisfactory when the ash has one or two components. However, such a system generally will not achieve satisfactory results when the ash contains three components.

OBJECTS OF THE INVENTION

An object of the present invention is to provide a system and process for determining the percentage of ash in paper when the ash comprises three components.

Further objects and advantages of the invention can be ascertained by reference to the specification and drawings herein which are by way of example only and not in limitation of the invention which is defined by the claims and equivalents thereto.

DETAILED DESCRIPTION OF THE PREFERRED EMBODIMENT

Figure 1:
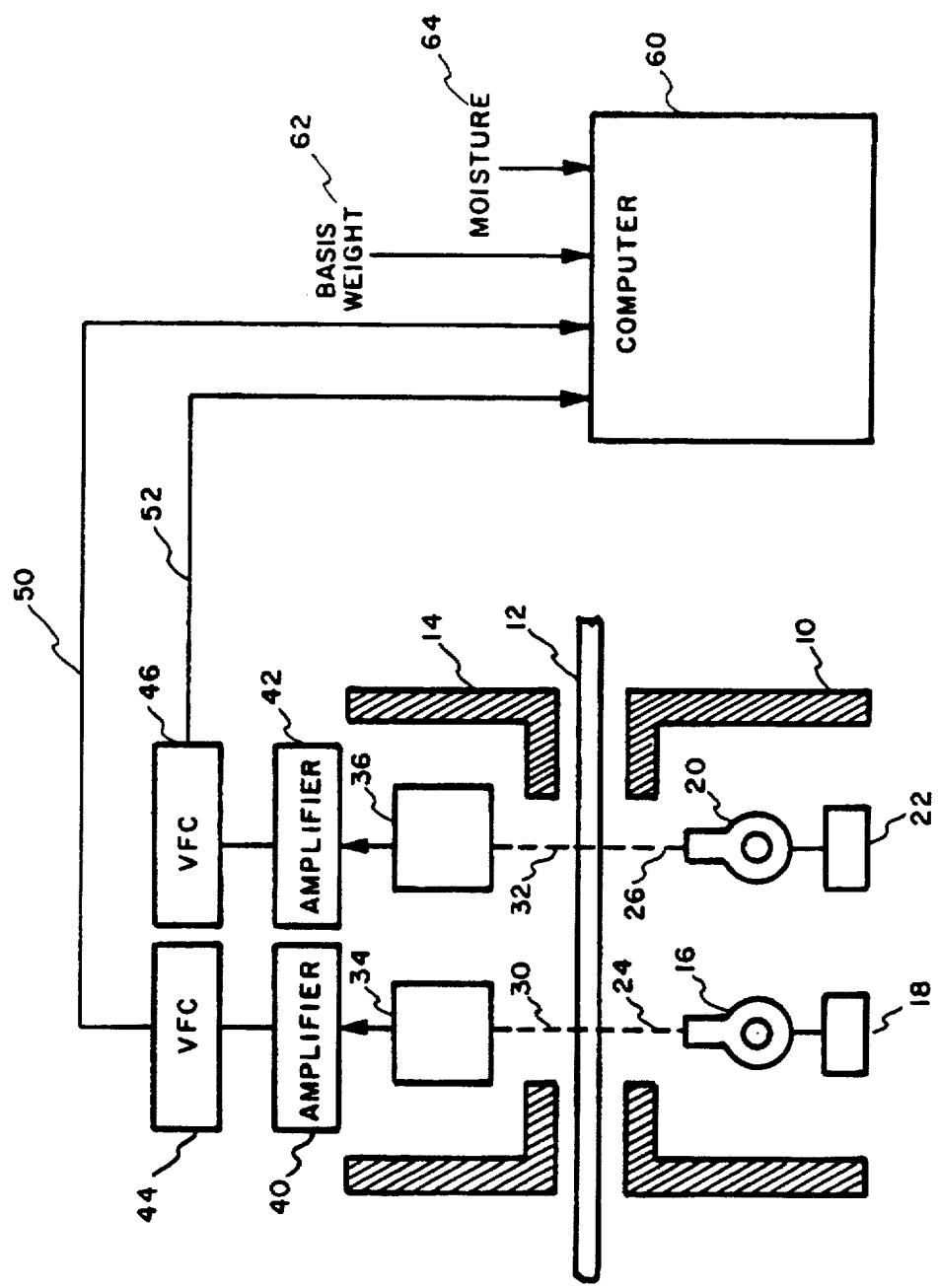
FIG. 1 is a schematic illustration, partially in cross section, of a system according to the preferred embodiment of the present invention.

With reference to FIG. 1, the preferred embodiment includes a source housing 10 located to one side of a moving sheet of paper 12. A detector housing 14 is located on the side of the paper 12 opposite the source housing 10, and both housings 10 and 14 are constructed and arranged to be movable in synchronized fashion across the sheet of paper 12 so that measurements of ash can be made across the sheet of paper. Various types of conventional scanning systems are available to move the housings 10 and 14.

The source housing 10 contains two x-ray sources, the first source including an x-ray tube 16 coupled to a power supply 18 and a second x-ray tube 20 coupled to a second power supply 22. The first and second x-ray tubes 16 and 20 generate first and second x-ray beams 24 and 26, respectively. The portion of the first x-ray beam 24 which passes through the paper is designated as beam 30, and the portion of the second x-ray beam 26 which passes through the paper 12 is designated as 32.

The detector housing 14 contains a first x-ray detector 34 which is mounted to receive the beam 30, and a second x-ray detector 36 mounted to receive the beam 32. In practice the detectors 34 and 36 can be krypton-filled ion chambers with beryllium windows so that the x-rays received by the detectors generate small currents in the ion chamber. The current is proportional to the strength of the x-ray beam entering the chamber. The two detectors 34 and 36 are electrically coupled to amplifiers 40 and 42 which generate analog type electrical signals proportional to the signals from the detector. The amplifiers 40 and 42 are electrically coupled to voltage-to-frequency converters 44 and 46 which convert the analog signals from the amplifiers into digital signals to be transmitted over lines 50 and 52 to a computer 60.

The computer 60 is coupled to receive signals representing the basis weight of the paper 62 and the moisture of the paper 64. The basis weight and moisture signals can be generated by conventional devices.

Figure 2:
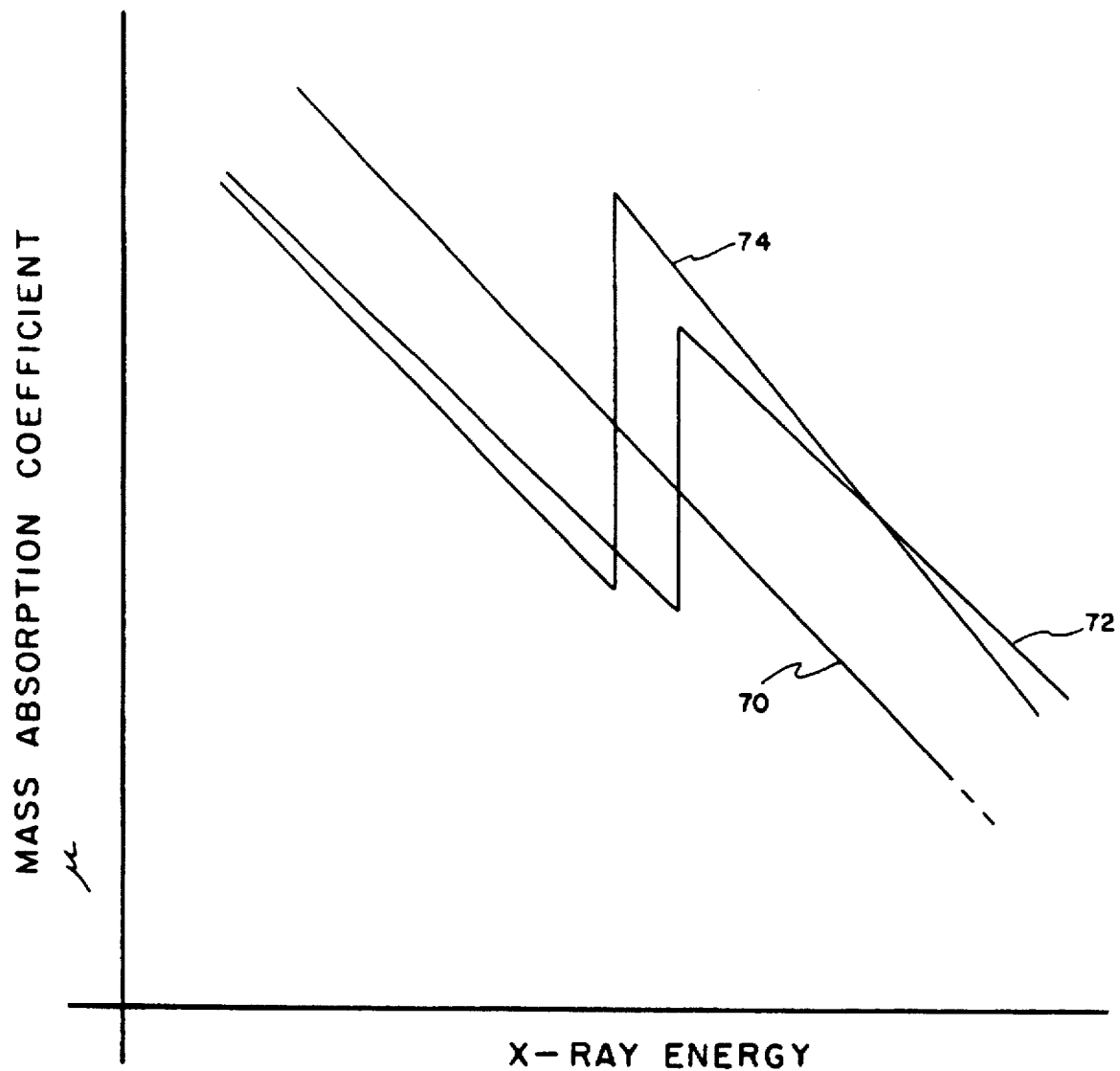
FIG. 2 is a graph showing the x-ray energy vs. the mass absorption coefficient, $\mu$, for three constituents of ash.

In FIG. 2 there is shown a plot of x-ray energy vs. mass absorption coefficient, $\mu$, for three constituents of ash, namely clay indicated by line 70, titanium dioxide ($TiO_2$), indicated by line 72 and calcium carbonate ($CaCO_3$)) indicated by line 74. The x-ray energy is normally measured in thousands of electron volts, KeV, and the mass absorption coefficient, $\mu$, is normally measured in units of square centimeters per gram, $Cm^2/g$. It should be understood that the graph in FIG. 2 is not intended to be to any particular scale, nor is it intended to be completely accurate. However, the important feature of the graph which is intended to be illustrated is the relative locations of the curves for the three components and the locations of the discontinuities in the graphs 72 and 74. The discontinuities in the two graphs are located at the so called K edges, and the K edge for graph 72 is at about 5 KeV; whereas the K-edge for the curve 74 is located at about 4 KeV.

In operation of the present system, the first x-ray tube 16 is constructed to generate x-rays having an evergy above the K-edges for both titanium dioxide and calcium carbonate. A preferred energy is about 7 KeV. The second x-ray tube 20 is constructed to generate x-rays having an energy below the K-edge for both titanium dioxide and calcium carbonate. A preferred energy is about 3.9 KeV. We have found that a satisfactory method of generating x-rays in these ranges is to construct the first x-ray tube with a tungsten target and to set the anode voltage to 7 KeV. This produces a Brenstrahlung spectrum of x-rays with a maximum energy determined by the anode voltage. The low energy x-rays are removed by placing a suitable "filter" consisting of a steel or aluminum sheet of calculated thickness in front of the source. This allows tuning the x-ray energy to the proper range. Alternatively, a cobalt target x-ray tube could be used to produce mono-energetic x-rays of about 8 KeV. This would eliminate the need for filtering.

The second x-ray tube 20 preferably uses a tungsten target with the anode voltage set below the K-edge energy, preferably about 3.9 KeV. No filtering is required with respect to this tube since all the x-rays have energies below the K-edge.

The equations required to determine the ash content are as follows:

For the signal from the first detector 34:

$$R1 = e^{-(\mu_1 w_1 + \mu_2 w_2 + \mu_3 w_3 + \mu_f w_f + \mu_w w_w)} \qquad (\text{Eq. 1})$$

where

R1=ratio of signal in the presence of the paper to signal in the absence of the paper.

$\mu_1$=mass absorption coefficient of ash component 1 ($TiO_2$)

$w_1$=weight per unit area of ash component 1

$\mu_2$=mass absorption coefficient of ash component 2 ($CaCO_3$)

$w_2$=weight per unit area of ash component 2

$\mu_3$=mass absorption coefficient of ash component 3 (Clay)

$w_3$=weight per unit area of ash component 3

$\mu_f$=mass absorption coefficient of paper fiber $w_f$=weight per unit area of paper fiber $\mu_w$=mass abosorption coefficient of water $w_w$=weight per unit area of water (Moisture or MOI)

The x-ray energy on the first x-ray tube 16 is chosen such that:

$\mu_1 \cong \mu_2 >> \mu_3$

For the signal from the second detector 36:

$$R2 = e^{-(\mu'_1 w_1 + \mu'_2 w_2 + \mu'_3 w_3 + \mu'_f w_f + \mu'_w w_w)} \qquad (\text{Eq. 2})$$

where the variables are defined as for Eq. 1 except that the mass absorption coefficients $\mu$ have values different from $\mu$ because the x-ray energy is different. The x-ray energy of the second tube is chosen such that:

$\mu'_1 \cong \mu'_2 << \mu'_3$

Furthermore, the following equations are known:

$$BW = w_1 + w_2 + w_3 + w_f + w_w \qquad (\text{Eq. 3})$$

where BW is the basis weight or weight per unit area of the sheet of paper 12, i.e.:

$$w_f = BW - w_1 - w_2 - w_3 - w_w \qquad (\text{Eq. 4})$$

Calculations:

Take the log of both sides of Eqs. 1 and 2 and substitute Eq. 4 for $w_f$ $$-\ln R1 = (\mu_1 - \mu_f) w_1 + (\mu_2 - \mu_f) w_2 + (\mu_3 - \mu_f) w_3 + \mu_f BW + (\mu_w - \mu_f) w_w \quad (\text{Eq. 5})$$

$$-\ln R2 = (\mu'_1 - \mu'_f) w_1 + (\mu'_2 - \mu'_f) w_2 + (\mu'_3 - \mu'_f) w_3 + \mu'_f BW + (\mu'_w - \mu'_f) w_w \quad (\text{Eq. 6})$$

The values of BW and $w_w$ are provided by a basis weight sensor and a moisture sensor which are standard components of a paper measurement system.

By taking advantage of the $\mu$ values provided by the energy selection criteria we can define the following constants:

$A = \mu_1 - \mu_f \cong \mu_2 - \mu_f$ $B = \mu_3 - \mu_f$ $C = \mu_w - \mu_f$ $D = \mu_f$ and $A' = \mu'_1 - \mu'_f \cong \mu'_2 - \mu'_f$ $B' = \mu'_3 - \mu'_f$ $C' = \mu'_w - \mu'_f$ $D' = \mu'_f$ also it is usual to use the fractional ash content $f_1 = w_1/BW$ $f_2 = w_2/BW$ $f_3 = w_3/BW$ $MOI = w_w/BW$ Thus, $$\frac{-\ln R1}{BW} = A(f_1 + f_2) + Bf_3 + C\,MOI + D \qquad (\text{Eq. 7})$$

$$\frac{-\ln R2}{BW} = A'(f_1 + f_2) + B'f_3 + C'\,MOI + D' \qquad (\text{Eq. 8})$$

From Eqs. 7 and 8 the values of $f_1 + f_2$ and $f_3$ can be determined.

$$f_1 + f_2 = \frac{-1}{A'B - AB'} \left[ \frac{B}{BW} \ln R2 - \frac{B'}{BW} \ln R1 + \right. \qquad (\text{Eq. 9})$$

$$\left. (BC - B'C)MOI + (B'D - BD') \right]$$

$$f_3 = \frac{-1}{A'B - AB'} \left[ \frac{A}{BW} \ln R2 - \frac{A'}{BW} \ln R1 + \right. \qquad (\text{Eq. 10})$$

$$\left. (A'C - AC')MOI + (A'D - AD') \right]$$

The total fractional ash content is $$f_T = f_1 + f_2 + f_3 \quad \text{(Eq. 11)}$$

$$= \frac{1}{A'B - AB'}\left[\frac{B-A}{BW}\ln R2 - \frac{B'-A'}{BW}\ln R1 + (B'-A')C - ((B-A)C')MOI + ((B'-A')D - (B-A)D')\right]$$

At this point it is convenient to regroup the constants into a set of linear coefficients.

$$C0 = 100\frac{(B'-A')D - (B-A)D'}{A'B - AB'}$$

$$C1 = 100\frac{A'-B'}{A'B - AB'}$$

$$C2 = 100\frac{B-A}{A'B - AB'}$$

$$C3 = 100\frac{(B'-A')C - (B-A)C'}{A'B - AB'}$$

Thus total percent ash is $$\% \text{ASH} = C0 + C1\frac{\ln R1}{BW} + C2\frac{\ln R2}{BW} + C3\, MOI \quad \text{(Eq. 12)}$$

In practice the coefficients C0, C1, C2 and C3 are determined by first analyzing samples of paper containing various amounts of the ash to determine a plurality of values of R1 and R2. Standard laboratory methods are used to determine BW, MOI and percent ash. Then the coefficients are determined using multiple linear regression.

It should be understood that although FIG. 2 concerns an ash having three components, the present process can be applied to an ash having more than three components. For example, if the ash contains a fourth component, talc, the graph of x-ray energy versus mass absorption coefficient for the talc would be almost the same as the graph for clay, and the present process would be applicable. Thus, the present process is applicable to a mixture containing at least three materials. In such a case the first beam must have an energy above K-edges of at least two of the materials and the second beam must have an energy below the K-edges of the same at least two materials.

We claim:

1. A process for determining the concentration of a first component of a mixture wherein the first component includes at least three materials, said process comprising:
   a) directing two beams of x-rays into the mixture, at least one beam having a spectrum of x-rays having a plurality of different energies, the first beam including x-rays having an energy above the K-edges of at least two of the materials and the second beam including x-rays having an energy below the K-edges of the same at least two materials, wherein the energy distributions of the two beams are different and are such that, for each beam, the mass absorption coefficient for the same two materials is substantially equal, but different from the mass absorption coefficient for the third material;
   b) receiving the portions of said two beams which are transmitted through the mixture; and
   c) determining the concentration of the first at least three material component based upon the two directed beams and the transmitted portion of the two beams, and not based upon any other x-ray beams.

2. A process according to claim 1 wherein said at least three materials include clay, titanium dioxide and calcium carbonate.

3. A process according to claim 1 wherein the first beam has an energy of about 7 KeV and the second beam has an energy of about 3.9 KeV.

4. A process according to claim 1 wherein said first component is ash and the mixture is paper.

5. A process according to claim 1 wherein the K-edges for two of said materials are near one another.

6. A process according to claim 1 wherein:
   a) the first component consists of three materials;
   b) the first beam has an energy above the K-edges of two of said materials;
   c) the mass absorption coefficients of said two materials are greater than the mass absorption coefficient of the third material at the energy of the first beam; and,
   d) the mass absorption coefficients of said two materials are less than the mass absorption coefficient of the third material at the energy of said second beam.

7. A system for determining the concentration of a mixture wherein the first component includes at least three materials, said system comprising:
   a) source means for producing two beams of x-rays and directing the beams into the mixture, at least one beam having a spectrum of x-rays having a plurality of energies, the first beam including x-rays having an energy above the K-edges of at least two of the materials and the second beam including x-rays having an energy below the K-edges of the same two materials, wherein the energy distributions of the two beams are different and are such that, for each beam, the mass absorption coefficient for the same two materials is substantially equal, but different from the mass absorption coefficient for the third material;
   b) means for receiving the portions of said two beams which are transmitted through the mixture; and
   c) means for determining the concentration of the first at least three material component based upon the two directed beams and the transmitted portions of the two beams and not based upon any other x-ray beams.

8. A system according to claim 7 wherein said source means includes means to produce the first beam, including a tungsten target x-ray tube with the anode voltage set above the K-edges of the two materials and a filter to remove x-rays below the K-edge.

9. A system according to claim 7 wherein said source means includes means to produce the second beam including a tungsten target x-ray tube with the anode voltage set below the K-edges of the two materials.

10. A system according to claim 7 wherein the first component is ash; the mixture is paper; and said means for determining the concentration of ash includes a computer to implement the following equation:

$$\text{Percent Ash} = C0 + C1\frac{\ln R1}{BW} + C2\frac{\ln R2}{BW} + C3(MOI)$$

where:
C0, C1, C2 and C3 are constants,
R1 and R2 are functions of the mass absorption coefficients of the ash,
BW=Basis weight of the paper
MOI=Moisture of the paper.

11. A process for determining the amount of a first component of a mixture wherein the first component includes variable proportions of three materials, said process comprising the steps of:
   a) directing a first x-ray beam into the mixture, the first x-ray beam having a first spectrum of x-rays having a plurality of energies, the energy distribution of the first spectrum being such that the mass absorption coefficient for the first material is substantially equal to the mass absorption coefficient for the second material and different from the mass absorption coefficient for the third material;

b) directing a second x-ray beam into the mixture, the second x-ray beam having a second spectrum of x-rays having a plurality of energies, the energy distribution of the second spectrum being such that the mass absorption coefficient for the first material is substantially equal to the mass absorption coefficient for the second material and different from the mass absorption coefficient for the third material, the energy composition of the second x-ray beam being different that the energy composition of the first x-ray beam;

c) receiving the portions of said first and second x-ray beams which are transmitted through the mixture; and d) determining the amount of the first component based upon the two directed x-ray beams and the transmitted portions of the two x-ray beams.

12. A process according to claim 11, wherein the three materials are titanium dioxide, calcium carbonate and clay, and wherein the mixture is paper.

13. A process according to claim 11, wherein the mass absorption coefficients of the first and second materials are greater than the mass absorption coefficient of the third material at the energies of the first x-ray beam and the mass absorption coefficents of the first and second materials are less than the mass absorption coefficient of the third material at the energies of the second x-ray beam.

14. A system for determining the amount of a first component of a mixture, wherein the first component includes variable proportions of first, second and third materials, the system comprising:

a) sources of first and second incident x-ray beams for directing the beams into the mixture, the first and second beams each having a different spectrum of x-rays having a plurality of energies, the beams being such that, for both the first and the second beams, the mass absorption coefficient of the first material is substantially equal to the mass absorption coefficient of the second material but different from the mass absorption coefficient of the third material;

b) detectors for detecting the portions of the incident first and second beams which are transmitted through the mixture and for generating signals indicative of the intensities of the detected transmitted portions of the x-ray beams; and C) computing means operatively coupled to the detectors for receiving the signals and computing the amount of the first component based upon the signals.

15. A system according to claim 14, wherein the source of the first incident x-ray beam includes a tungsten target x-ray tube with an anode voltage set above the K-edges of the first and second materials and a filter to remove x-rays below the K-edge of the first material such that the mass absorption coefficents of the first and second materials are substantially equal.

16. A system according to claim 14, wherein the first component is ash, the mixture is paper and the computing means is a computer programmed to implement the following equation:

$$\% \text{ ash} = C0 + C1(\ln R1/BW) + C2(\ln R2/BW) + C3\ (MOI),$$

where,

C0, C1, C2 and C3 are constants;

R1 and R2 are functions of the mass absorption coefficients of the ash;

BW is the basis weight of the paper, and

MOI is the amount of moisture in the paper.

17. A system according to claim 14, wherein the first material is titanium dioxide, the second material is calcium carbonate and the third material is clay.

18. A system for determining the composition of a component in a mixture, wherein the component includes variable proportions of at least first, second and third materials, the system comprising:

a) sources of first and second incident x-ray beams for directing the beams into the mixture, the first and second x-ray beams each having a different spectrum of x-rays having a plurality of energies, the beams being such that, for both the first and second beams, the mass absorption coefficient of the first material is substantially equal to the mass absorption coefficient of the second material but different from the mass absorption coefficient of the third material;

b) detectors for detecting the portions of the incident first and second beams which are transmitted through the mixture and for generating signals indicative of the intensities of the detected transmitted portions of the x-ray beams; and c) computing means operatively coupled to the detectors to receive the signals and to compute the amount of the third material in the at least three material component based upon the signals.

19. A system according to claim 18, wherein the mixture is paper sheet, the component is ash, the system further comprising a sheet moisture sensor and a sheet basis weight sensor, wherein the moisture sensor and basis weight sensor are operatively coupled to the computing means and the computing means computes the amount of the third material in the at least three material component based upon the sensed basis weight and moisture in addition to the signals.

20. A system according to claim 18, wherein the computing means further computes the combined amount of the first and second materials in the at least three material component based upon the signals.

21. A system according to claim 20, wherein the mixture is paper sheet and the component is ash, the system further comprising a sheet moisture sensor and a sheet basis weight sensor, wherein the moisture sensor and the basis weight sensor are operatively coupled to the computing means and the computing means computes the combined amount of the first and second materials in the at least three component material based upon the sensed basis weight and moisture in addition to the signals.

22. A system according to claim 20, wherein the computing means further computes the combined amounts of the first, second and third materials.

23. A system according to claim 22, wherein the first material includes titanium dioxide, the second material includes calcium carbonate and the third material includes clay.

24. A process for determining the concentration of a first component of a mixture wherein the first component includes at least three materials, said process comprising:

a) producing first and second beams of x-rays, at least one beam having a spectrum of x-rays having a plurality of different energies;

b) producing or filtering at least one of the energy spectra of the first and second beams such that the energy distributions of the first and second beams are different and such that, for each of the first and second beams, the mass absorption coefficients for the same two materials are substantially equal, but different from the mass absorption coefficient for the third material;

c) directing the first and second beams into the mixture;

d) receiving the portions of the first and second beams which are transmitted through the mixture; and e) determining the concentration of the first at least three material component based upon the first and second beams and the transmitted portion of the two beams, and not based upon any other x-ray beams.

25. A system for determining the concentration of a first component of a mixture wherein the first component includes at least three materials, said system comprising:

a) source means for producing first and second beams of x-rays, at least one beam having a spectrum of x-rays having a plurality of energies;

b) means for producing or filtering the energy spectra of at least one of the first and second beams such that the energy distributions of the first and second beams are different and such that, for each of the first and second beams, the mass absorption coefficients for the same two materials are substantially equal, but different from the mass absorption coefficient for the third material;

c) means for directing the first and second beams into the mixture;

d) means for receiving the portions of the first and second beams which are transmitted through the mixture; and e) means for determining the concentration of the first at least three material component based upon the two directed beams and the transmitted portions of the two beams, and not based upon any other x-ray beams.

* * * * *